(12) United States Patent
Kudo et al.

(10) Patent No.: US 8,591,490 B2
(45) Date of Patent: Nov. 26, 2013

(54) ABSORBENT ARTICLE INCLUDING AN ABSORBENT ARTICLE MAIN BODY AND AN ABSORBENT BODY OVERLAPPING THE ABSORBENT ARTICLE MAIN BODY

(75) Inventors: Jun Kudo, Ehime (JP); Hideyuki Kinoshita, Kagawa (JP); Akira Hashino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 482 days.

(21) Appl. No.: 12/444,675

(22) PCT Filed: Nov. 19, 2007

(86) PCT No.: PCT/JP2007/072407
§ 371 (c)(1),
(2), (4) Date: May 12, 2009

(87) PCT Pub. No.: WO2008/062766
PCT Pub. Date: May 29, 2008

(65) Prior Publication Data
US 2010/0076392 A1    Mar. 25, 2010

(30) Foreign Application Priority Data

Nov. 20, 2006  (JP) ................................. 2006-313194
Nov. 20, 2006  (JP) ................................. 2006-313195

(51) Int. Cl.
*A61F 13/15* (2006.01)
*A61F 13/20* (2006.01)

(52) U.S. Cl.
USPC ............ 604/385.16; 604/385.01; 604/385.11; 604/385.101

(58) Field of Classification Search
USPC ........... 604/385.01, 385.03, 385.101, 385.11, 604/385.14, 385.16
See application file for complete search history.

(56) References Cited

U.S. PATENT DOCUMENTS

| | | | |
|---|---|---|---|
| 6,316,688 B1 * | 11/2001 | Hammons et al. | 604/378 |
| 6,890,326 B2 * | 5/2005 | White | 604/385.17 |
| 7,648,490 B2 * | 1/2010 | Kuroda et al. | 604/385.01 |
| 8,444,618 B2 * | 5/2013 | Kudo et al. | 604/385.11 |
| 2002/0193766 A1 * | 12/2002 | Gell et al. | 604/385.03 |
| 2008/0015538 A1 * | 1/2008 | Deerin | 604/402 |
| 2008/0172019 A1 * | 7/2008 | Chien | 604/385.04 |
| 2010/0121303 A1 * | 5/2010 | Kudo et al. | 604/385.201 |

(Continued)

FOREIGN PATENT DOCUMENTS

| | | |
|---|---|---|
| EP | 1048277 A2 | 11/2000 |
| EP | 1048277 A3 | 9/2001 |

(Continued)

OTHER PUBLICATIONS

Certified Translation of Reference to Higuchi (JP 2002-159534).*

(Continued)

*Primary Examiner* — Michele M Kidwell
(74) *Attorney, Agent, or Firm* — Lowe Hauptman & Ham, LLP

(57) ABSTRACT

To provide an absorbent article that is small and can effectively absorb fluid.
The absorbent article includes: an absorbent body having a fluid-absorbent member for absorbing fluid; and an absorbent article main body on which the absorbent body is overlapped with along a longitudinal direction, in which the fluid-absorbent member of the absorbent body is projected in the longitudinal direction from an outer circumferential edge of the absorbent article main body.

15 Claims, 15 Drawing Sheets

(56) References Cited

U.S. PATENT DOCUMENTS

| | | | | |
|---|---|---|---|---|
| 2010/0280475 | A1* | 11/2010 | Kudo et al. | 604/380 |
| 2011/0046596 | A1* | 2/2011 | Kudo et al. | 604/385.24 |
| 2012/0010586 | A1* | 1/2012 | Kudo et al. | 604/378 |

FOREIGN PATENT DOCUMENTS

| | | | |
|---|---|---|---|
| JP | 53-97540 | A | 8/1978 |
| JP | 5397540 | | 8/1978 |
| JP | 08-000664 | A | 1/1996 |
| JP | 10-286278 | A | 10/1998 |
| JP | 10286278 | | 10/1998 |
| JP | 2002-159534 | A | 6/2002 |
| JP | 2002159534 | | 6/2002 |
| JP | 2004-284201 | A | 10/2004 |
| JP | 2005312557 | | 11/2005 |
| WO | 02062278 | A1 | 8/2002 |

OTHER PUBLICATIONS

PCT/JP2007/072407 International Search Report.
Japanese Office Action for Application No. 2006-313194 mailed Nov. 8, 2011.
Japanese Office Action for Application No. 2006-313195 mailed Nov. 8, 2011.
Extended European Search Report for Application No. 07832137.9 mailed May 31, 2012.

* cited by examiner

ABSORBENT ARTICLE INCLUDING AN ABSORBENT ARTICLE MAIN BODY AND AN ABSORBENT BODY OVERLAPPING THE ABSORBENT ARTICLE MAIN BODY

RELATED APPLICATIONS

The present application is based on, International Application PCT/JP2007/072407, filed Nov. 10, 2007, which claims priority from, Japanese Application Numbers 2006-313194 and 2006-313195, both filed Nov. 20, 2006, the disclosures of which are hereby incorporated by reference herein in their entirety.

TECHNICAL FIELD

The present invention relates to absorbent articles for absorbing fluid.

BACKGROUND ART

Conventionally, as absorbent articles that absorb certain fluid such as menstrual blood, absorbent articles including a main body section that absorbs fluid and a surface structure partially fixed to the surface of the main body section, in which the back face of the main body section includes a fluid-impermeable sheet made of polyethylene or the like in order to prevent leakage of the fluid are known (refer to JP-A-2003-79662, for example). Regarding the above fluid, the manner of the flow varies depending on the posture of the user when wearing the absorbent article. For example, in the case where the body is in a standing state, fluid flows in the vertical direction and is often directly absorbed by the absorbent article. However, in a state the body is lying down during sleep or the like, discharged fluid may flow down the body, more specifically, the bodily groove, and flow towards the rear side of the user. Accordingly, in order to cause fluid to be absorbed without leakage at any time, there is needed an absorbent article that is large enough to cover an area from a position covering a front side of a fluid discharge portion to a position covering the bodily groove, such as the vicinity of the coccyx.

Further, in recent years, in order to prevent displacement, an absorbent article has been devised including a surface structure that is disposed along the front-and-rear direction of the body in use, and that has a front side fixed to a main body section and a rear side separable from the main body section, and the absorbent article is worn so that the rear side portion of the surface structure is in the groove between the buttocks. At the time of using the absorbent article, the user pulls up the rear end side of the surface structure rearward, thereby disposing the surface structure in the groove between the buttocks.

DISCLOSURE OF INVENTION

Problems to be Solved by the Invention

The foregoing conventional absorbent article can suppress leakage by absorbing discharged fluid in its wide region regardless of the posture of the user. However, since the absorbent article itself is large in size, there is the problem that its portability is poor.

Furthermore, in the conventional absorbent article, in the case only the front portion of the surface structure is fixed, the position of the rear end section of the surface structure is unstable, and since it is difficult for the user to catch the rear end section of the surface structure, it is desirable that until use the rear end section is temporarily fixed to the main body section in a detachable manner. When using the foregoing conventional absorbent article, the user has to hold the rear end section of the surface structure in order to pull up the rear end side of the surface structure. Further, in a case where the rear end section of the surface structure is temporarily fixed to the main body section, the temporary fixation has to be released, and therefore the rear end section needs to be reliably held by the user. When the rear end section of the surface structure is projected from the main body section, and the surface structure is temporarily fixed to the main body section at the position where the surface structure is overlapped with the rear end section of the main body section, the projected section can be easily held. However, when the rear end section of the surface structure is projected from the main body section, the total length of the absorbent article becomes longer, its size increases even in a wrapped state, and thus there is a problem that portability of the absorbent article may be impaired.

The present invention has been contrived in view of the above conventional issues, and it is an object thereof to provide an absorbent article that is small and can effectively absorb fluid, or an absorbent article that is small and highly absorbent.

Means for Solving the Problems

A first primary aspect of the invention for solving the above-described problem is an absorbent article that is worn on a body and used, including: an absorbent article main body having a longitudinal direction, a width direction perpendicular thereto, and a thickness direction perpendicular thereto; and an absorbent body having a fluid-absorbent member for absorbing fluid, wherein the absorbent body is overlapped, along the longitudinal direction, with a surface side of the absorbent article main body, the surface side being located on the side of the body at the time of use on the absorbent article main body, and the fluid-absorbent member of the absorbent body is projected outward in the longitudinal direction from an outer circumferential edge of the absorbent article main body.

A second primary aspect of the invention for solving the above-described problem is an absorbent article that is worn on a body and used, including: an absorbent article main body having a longitudinal direction, a width direction perpendicular thereto, and a thickness direction perpendicular thereto; and an absorbent body having a fluid-absorbent member for absorbing fluid, wherein the absorbent body is overlapped, along the longitudinal direction, with a surface side of the absorbent article main body, the surface side being located on the side of the body at the time of use on the absorbent article main body, and the absorbent body has a portion folded independently and separately from the absorbent article main body.

Effects of the Invention

According to the present invention, it is possible to provide an absorbent article that is small and can effectively absorb fluid, or an absorbent article that is small with high absorbency.

Figure 1:
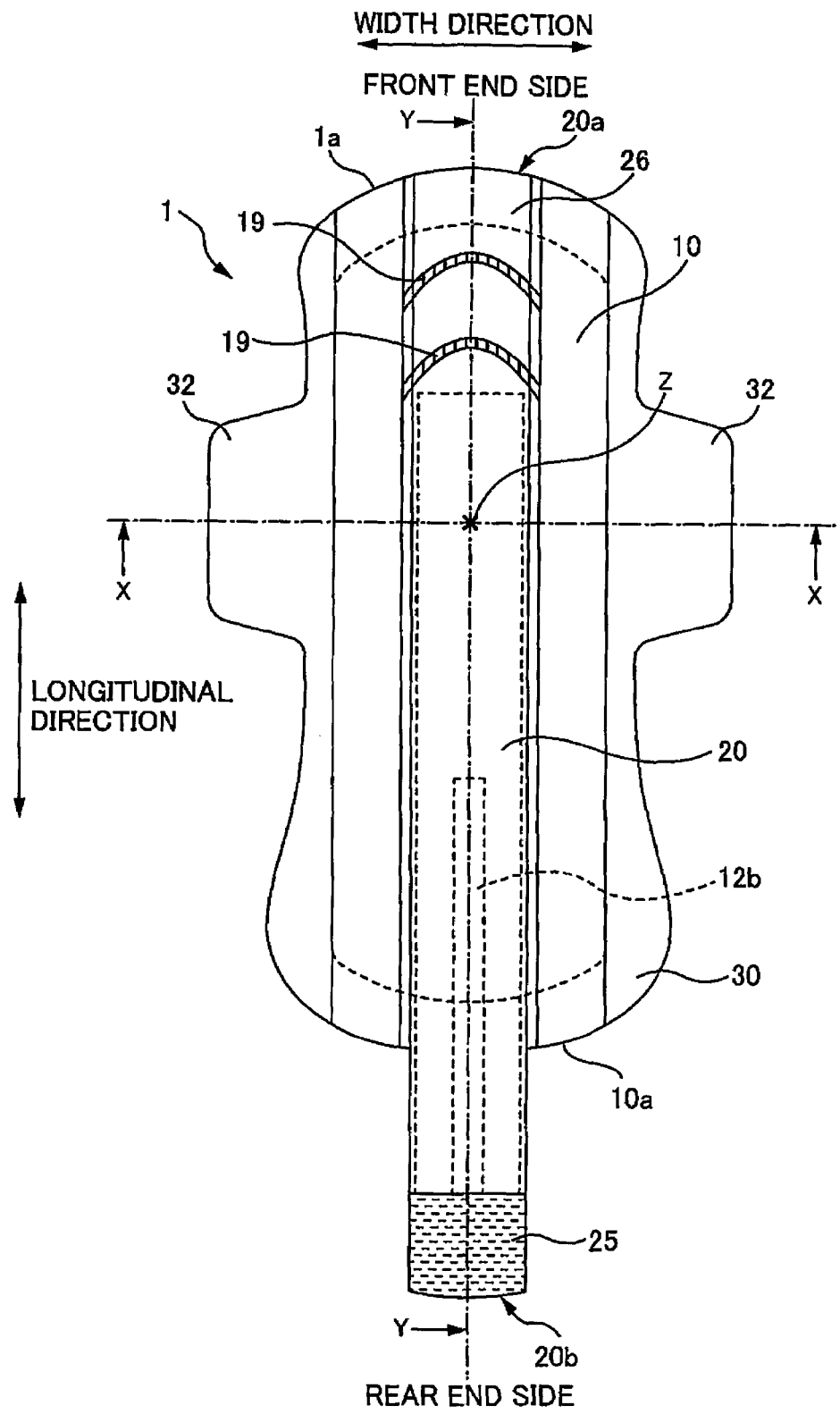
FIG. 1 is a plan view showing a surface side of an absorbent article according to a first embodiment.

LIST OF REFERENCE NUMERALS 1 absorbent article, 1a front end, 2 absorbent article, 3 absorbent article, 10 base absorbent body (absorbent article main body), 12 absorbent body base material, 12a absorbent body material (fluid-absorbent member), 12b thin wall section, 12c folded portion, 14 surface sheet, 16 intermediate sheet, 19 deep-groove embossed pattern, 20 top absorbent body (absorbent body), 20a front end, 20b rear end, 22 hook member, 25 reinforced section, 25a grasping section, 26 reinforced section, fluid-impermeable sheet, 30 back face sheet, 32 holding section, 34 release sheet, 35 adhesive, 36 wrapping sheet, 36a front end, 36b rear end, 36c edge section, 38 lead tape, P folding position, Q folding position, R folding position, S folding position, Z position assumed to abut against the bodily discharge opening portion Best Mode For Carrying Out The Invention At least the following matters will be disclosed in the present specification and the drawings.

An absorbent article that is worn on a body and used, including: an absorbent article main body having a longitudinal direction, a width direction perpendicular thereto, and a thickness direction perpendicular thereto; and an absorbent body having a fluid-absorbent member for absorbing fluid, wherein the absorbent body is overlapped, along the longitudinal direction, with a surface side of the absorbent article main body, the surface side being located on the side of the body at the time of use on the absorbent article main body, and the fluid-absorbent member of the absorbent body is projected outward in the longitudinal direction from an outer circumferential edge of the absorbent article main body.

With such an absorbent article, the fluid-absorbent member of the absorbent body is projected outward along the longitudinal direction from the outer circumferential edge of the absorbent article main body. Thus, it is possible to make the projected absorbent body absorb fluid in a wider portion in the longitudinal direction than the absorbent article main body. At this time, the absorbent article main body is shorter in length than the absorbent body in the longitudinal direction. Thus, the absorbent article can be made smaller than in a case where the absorbent body and the absorbent article main body are formed equal in length. Accordingly, it is possible to realize an absorbent article that is small and can effectively absorb fluid.

In such an absorbent article, it is preferable that the width of the absorbent body in a direction that intersects the longitudinal direction is narrower than the width of the absorbent article main body in the direction that intersects the longitudinal direction. With such an absorbent article, since the narrow absorbent body is projected, it is possible to effectively absorb fluid by placing the absorbent body in a narrow width portion. Such an absorbent article is used, for example, for absorbing fluid such as menstrual blood. However, it is possible to cause fluid flowing down along the groove to be absorbed, by disposing the narrow absorbent body in and along the bodily groove.

In such an absorbent article, it is preferable that one end section in the longitudinal direction of the absorbent body is undetachably joined to the absorbent article main body, and the other end section in the longitudinal direction of the absorbent body is detachably joined to the absorbent article main body.

With such an absorbent article, by detaching the detachably joined other end section in the longitudinal direction of the absorbent body, the absorbent article can be in a state in which the absorbent body is joined to the absorbent article main body only at one end section. Furthermore, the portion on the side of the detached end section in the absorbent body can be separated from the absorbent article main body. Accordingly, for example, when using the absorbent article for the purpose of causing fluid such as menstrual blood to be absorbed, it is possible to cause fluid to be absorbed by separating the absorbent body from the absorbent article main body and placing it reliably in the bodily groove. Herein, "joining" includes undetachable joining (hereinafter, also referred to as "permanent joining") and detachable joining (hereinafter, also referred to as "temporary joining").

In such an absorbent article, it is preferable that before use, the fluid-absorbent member is not projected outward in the longitudinal direction from the outer circumferential edge of the absorbent article main body, and at the time of use, the other end section of the absorbent body is detached from the absorbent article main body, and the other end section is moved in the longitudinal direction by crossing over the one end section, and thus the fluid-absorbent member is projected outward from the outer circumferential edge of the absorbent article main body.

With such an absorbent article, the absorbent body is not projected from the absorbent article main body before use, that is, before the absorbent body is detached from the absorbent article main body. Further, the absorbent body detached from the absorbent article main body is moved toward the opposite side by crossing over the joined section on the side of the one end section in the longitudinal direction at the time of use, and thus the absorbent body is projected outward from the outer circumferential edge of the absorbent article main body. Accordingly, it is possible to realize an absorbent article that is small before the absorbent body is detached, and that can effectively absorb fluid with the absorbent body projected from the absorbent article main body after the absorbent body is detached.

In such an absorbent article, a portion of the absorbent body overlapped with the absorbent article main body may be undetachably joined.

With such an absorbent article, in the portion where the absorbent body and the absorbent article main body are overlapped, fluid that could not be absorbed with the absorbent body is received by the absorbent article main body, and thus a configuration in which fluid can be prevented from leaking out the absorbent article is realized. Moreover, fluid leaking along the longitudinal direction can be absorbed by the portion of the absorbent body projected from the absorbent article main body.

In such an absorbent article, it is preferable that a back face of the absorbent article main body includes a fluid-impermeable member, and in a portion of the absorbent body projected outward in the longitudinal direction from the outer circumferential edge of the absorbent article main body, a face of the side of the absorbent article main body includes a fluid-impermeable member.

With such an absorbent article, in the portion where the absorbent body and the absorbent article main body are overlapped, the fluid-impermeable member included on the back face of the absorbent article main body can prevent leakage of fluid from the absorbent body and the absorbent article main body. Furthermore, in the projected portion of the absorbent body, the leakage of fluid from the absorbent body and the absorbent article main body can be prevented with the fluid-impermeable member included on the face of the side of the absorbent article main body, in the portion of the absorbent body projected outward in the longitudinal direction from the outer circumferential edge of the absorbent article main body.

In such an absorbent article, it is preferable that the absorbent article main body includes another absorbent body that is different from the foregoing absorbent body.

With such an absorbent article, fluid can be absorbed by each of the absorbent article main body and the absorbent body. Such an absorbent article is used, for example, for absorbing fluid such as menstrual blood. However, it is possible to cause fluid flowing down along the groove to be absorbed by placing the narrow absorbent body along and in the bodily groove. Furthermore, it is possible to cause fluid flowing down in the vertical direction to be effectively absorbed with the absorbent body and the absorbent article main body.

Furthermore, an absorbent article that is worn on a body and used, including: an absorbent article main body having a longitudinal direction, a width direction perpendicular thereto, and a thickness direction perpendicular thereto; and an absorbent body having a fluid-absorbent member for absorbing fluid, wherein the absorbent body is overlapped, along the longitudinal direction, with a surface side of the absorbent article main body, the surface side being located on the side of the body at the time of use on the absorbent article main body, and the absorbent body has a portion folded independently and separately from the absorbent article main body.

With such an absorbent article, the absorbent body includes a portion folded independently and separately from the absorbent article main body. Thus, by unfolding the folded portion of the absorbent body, the absorbent body can absorb fluid in a wider portion than the absorbent article main body. Furthermore, by folding the absorbent body of the absorbent article independently, the size of the absorbent article can be made small. Accordingly, it is possible to realize an absorbent article that is small and can absorb fluid in a wider portion in the longitudinal direction. Herein, a "folded" state refers to not only a state in which a section is folded in the longitudinal direction to be overlapped one on another, but also a state in which a section is folded many times at short intervals in the longitudinal direction in a wavy form. Further, in a case where the section is finely folded, the "folded" state also refers to a state in which adjacent folded portions do not contact with each other, and a state in which the folded portions are not overlapped one on another.

In such an absorbent article, it is preferable that the width of the absorbent body in a direction that intersects the longitudinal direction is narrower than the width of the absorbent article main body in the direction that intersects the longitudinal direction.

With such an absorbent article, since the narrow absorbent body is projected, by placing the absorbent body in a narrow portion, fluid can be absorbed with the absorbent body in a wider region in the longitudinal direction than the absorbent article main body. Such an absorbent article is used, for example, for absorbing fluid such as menstrual blood. And the folded narrow absorbent body can be unfolded, and the unfolded absorbent body can be disposed along and in the bodily groove. Accordingly, fluid flowing down along the groove can be absorbed in a wider region in the longitudinal direction than the absorbent article main body. Furthermore, fluid flowing down in the vertical direction can be effectively absorbed by the absorbent article main body and the absorbent body.

In such an absorbent article, one end section in the longitudinal direction of the absorbent body is undetachably joined to the absorbent article main body, and the other end section in the longitudinal direction of the absorbent body is detachably joined to the absorbent article main body.

With such an absorbent article, the other end section of the absorbent body can be detached, and the absorbent body can be joined at only one end section. Furthermore, the portion on the side of the detached other end section can be separated from the absorbent article main body to be unfolded. Accordingly, for example, when using the absorbent article for absorbing fluid such as menstrual blood, this absorbent article is preferable as an absorbent article that absorbs fluid in which the absorbent body is separated from the absorbent article main body and reliably placed in the bodily groove. At that time, it is more preferable that the unfolded absorbent body is formed longer than the absorbent article main body. However, if the absorbent body is formed longer, the size of the absorbent article itself increases and its portability may be impaired. Thus, as in the above-described absorbent article, the absorbent body is folded independently and separately from the absorbent article main body, and thus the absorbent article with good portability can be realized.

Furthermore, since the absorbent body is folded, with the end section on the side of the folded portion temporarily joined in a detachable manner, it is possible to keep the absorbent body in a folded state. Also, it is possible to easily put the absorbent body into an unfolded state by detaching the temporarily joined portion.

In such an absorbent article, a portion of the absorbent body that overlaps with the absorbent article main body may be undetachably joined.

With such an absorbent article, in the portion where the absorbent body and the absorbent article main body are overlapped, fluid that could not be absorbed with the absorbent body is received with the absorbent article main body, and thus the configuration can be realized in which fluid is prevented from leaking out of the absorbent article. Moreover, fluid leaking along the longitudinal direction can be absorbed with the portion of the absorbent body projected from the absorbent article main body. At that time, since the absorbent body is formed longer than the absorbent article main body, the size of the absorbent article itself increases and its portability may be impaired. Thus, as in the above-described absorbent article, the portion of the absorbent body projected from the absorbent article main body is folded independently and separately from the absorbent article main body, and thus the absorbent article with good portability can be realized.

In such an absorbent article, it is preferable that the other end section of the absorbent body is folded toward the one end section side, and the folded portion is overlapped with another portion of the absorbent body.

With such an absorbent article, in the folded portion of the absorbent body, the other end section is folded toward the one end section side. Thus, the absorbent body can be folded neatly and more compactly.

In such an absorbent article, it is preferable that an end of the other end section of the absorbent body is oriented so as to be projected outward from an outer circumferential edge of the absorbent article main body.

With such an absorbent article, the end of the other end section of the absorbent body is oriented so as to be projected from the absorbent article main body. Thus, it is possible to easily unfold the folded absorbent body, merely by pulling the end section of the absorbent body in the longitudinal direction.

In such an absorbent article, it is preferable that in a state in which the absorbent body is folded, the absorbent article is worn so that the absorbent body in the folded state contacts against the body, and in a state in which the absorbent body is unfolded, the absorbent article is worn so that the absorbent body in the unfolded state contacts against the body.

Such an absorbent article can be in two states, namely a state in which the absorbent body is folded, and a state in which the absorbent body is unfolded and unfolded. Accordingly, for example, if fluid does not have to be absorbed in a wide range, the absorbent body can be used in the folded state, and if fluid has to be absorbed in a wide range, the absorbent body can be used as is in the unfolded state. Accordingly, the absorbent article can be used in two ways according to the application.

In such an absorbent article, it is preferable that the absorbent article main body includes a fluid-permeable surface sheet, a fluid-impermeable back face sheet, and the fluid-absorbent member interposed between the surface sheet and the back face sheet.

With such an absorbent article, fluid can be absorbed with the fluid-absorbent members respectively included in the absorbent article main body and the absorbent body.

Embodiments

First Embodiment of the Absorbent Article

First, the outline of the configuration of an absorbent article according to a first embodiment will be described. The absorbent article of this embodiment is a sanitary napkin. In the following explanation, the side that is brought into contact with the body is referred to as a surface side, the side that is brought into contact with an undergarment is referred to as a back face side, the end that is positioned on the front side of the human body when worn is referred to as a front end, and the end that is positioned on the rear side is referred to as a rear end.

Figure 2:
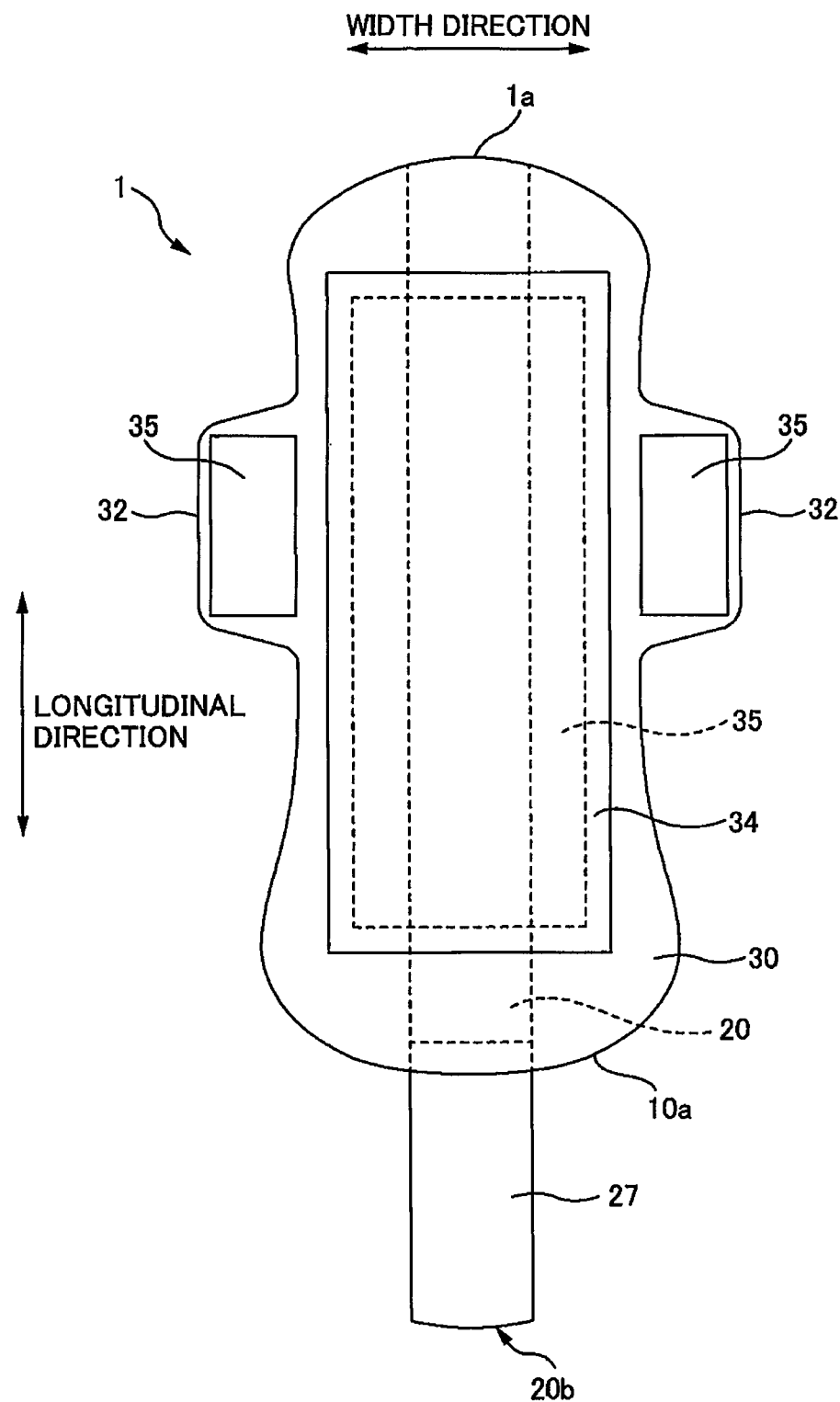
FIG. 2 is a view showing a back face side of the absorbent article according to the first embodiment.
Figure 3:
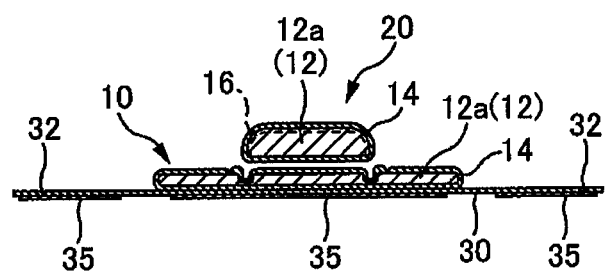
FIG. 3 is a cross-sectional view taken along line X-X in FIG. 1.
Figure 4:
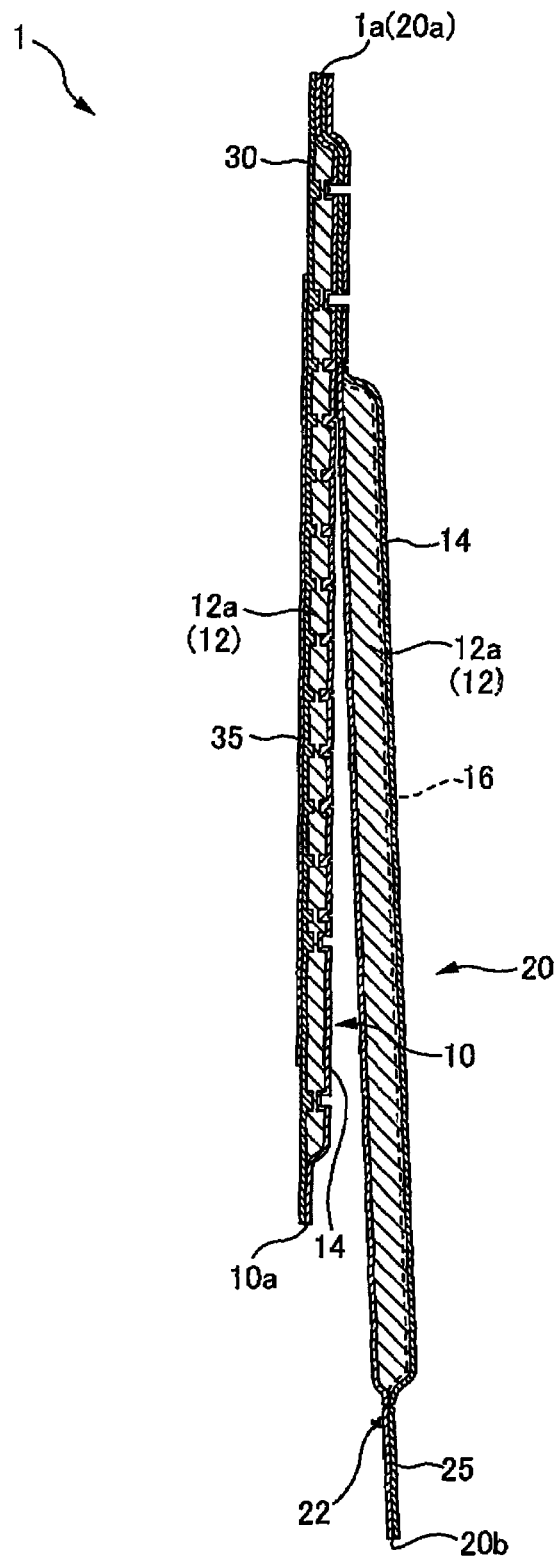
FIG. 4 is a cross-sectional view taken along line Y-Y in FIG. 1.
Figure 5:
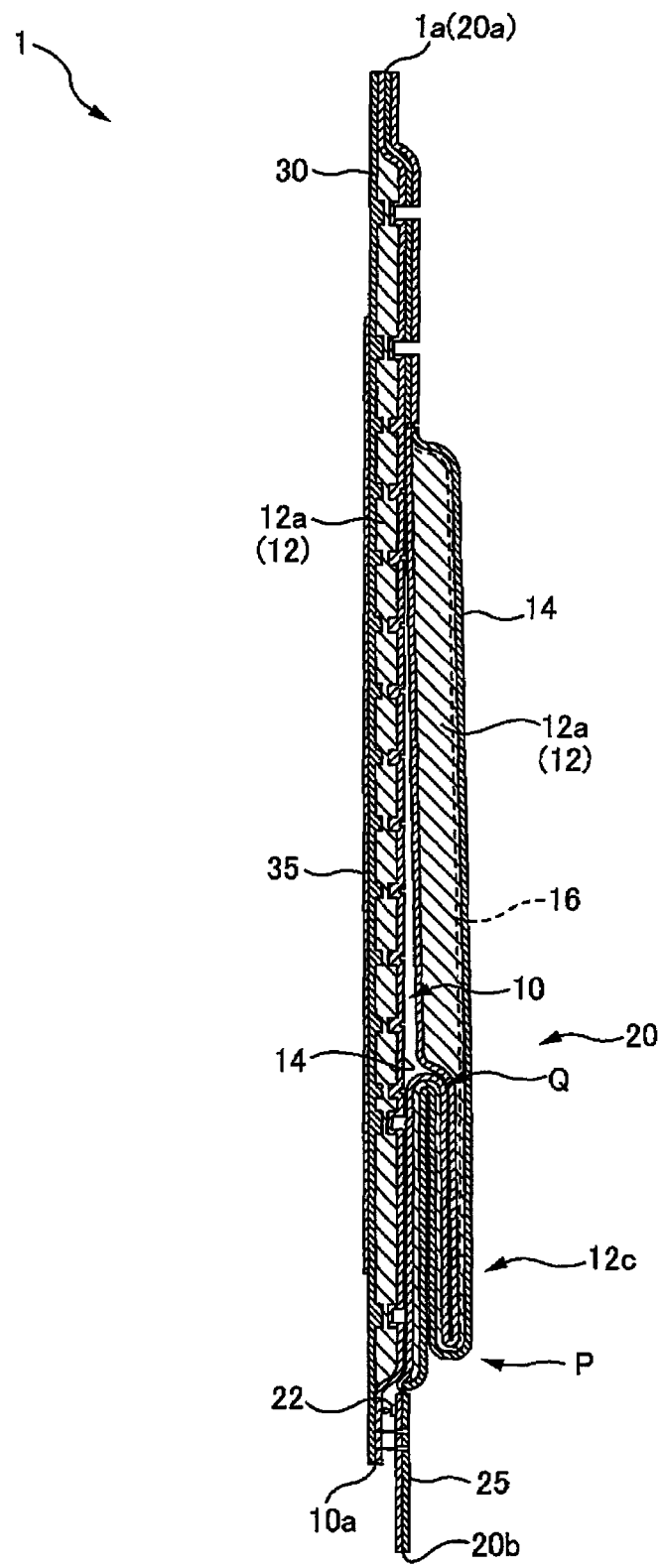
FIG. 5 is a cross-sectional view seen from Y-Y direction before use.
Figure 6:
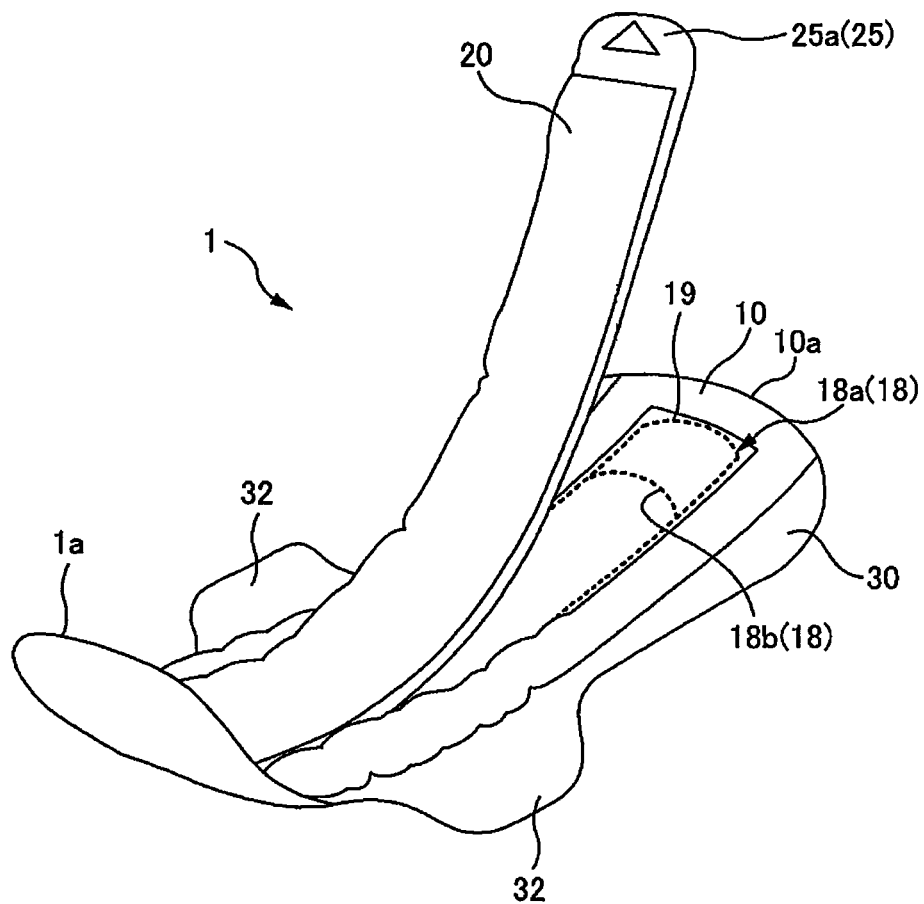
FIG. 6 is a perspective view showing the absorbent article according to the first embodiment.
Figure 7:
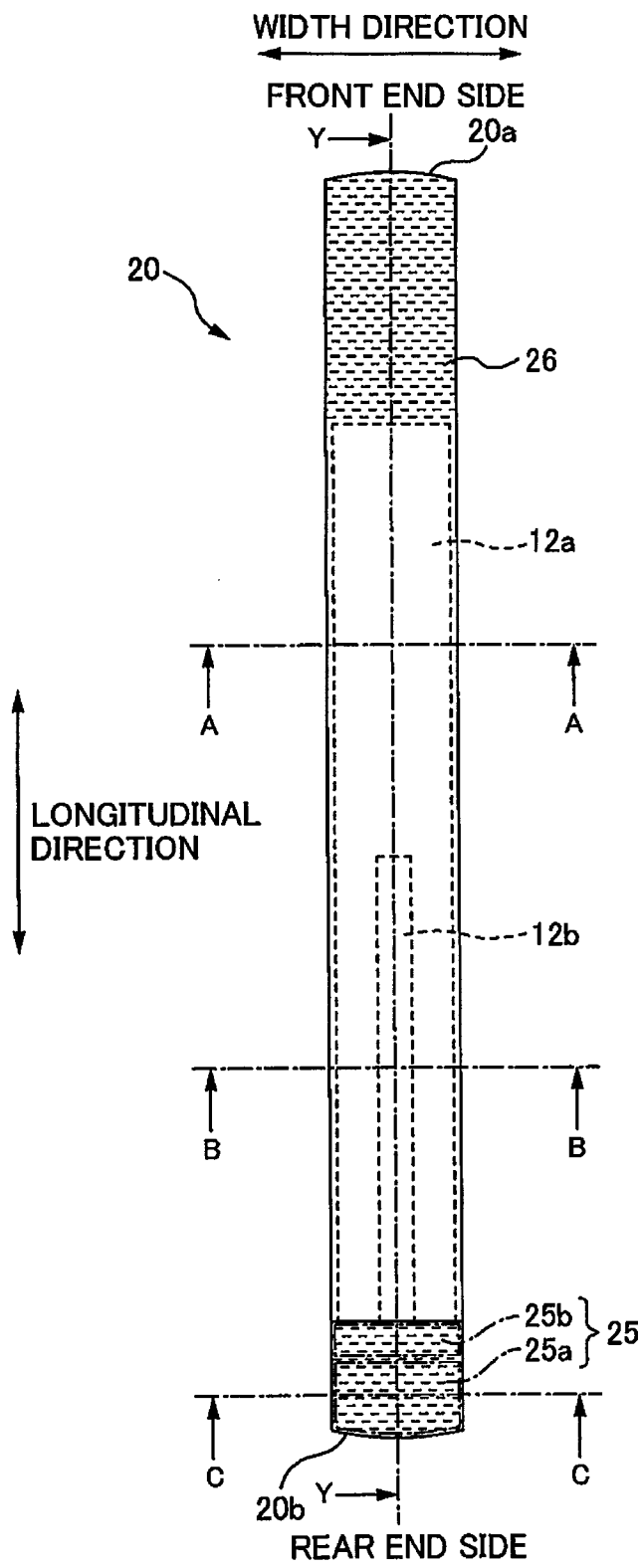
FIG. 7 is a plan view showing a top absorbent body.
Figure 8:
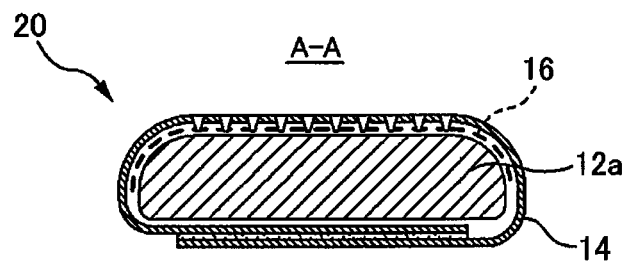
FIG. 8(a) is a cross-sectional view taken along line A-A in FIG. 7.
FIG. 8(b) is a cross-sectional view taken along line B-B in FIG. 7.
FIG. 8(c) is a cross-sectional view taken along line C-C in FIG. 7.
Figure 8:
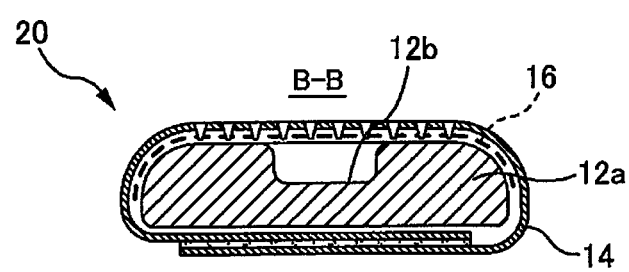
Figure 8:
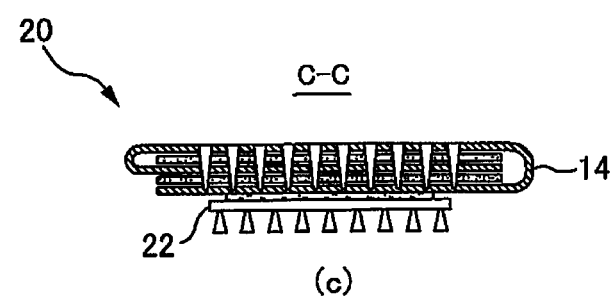

FIG. 1 is a plan view showing the surface side of the absorbent article according to the first embodiment. FIG. 2 is a view showing the back face side of the absorbent article according to the first embodiment. FIG. 3 is a cross-sectional view taken along line X-X in FIG. 1. FIG. 4 is a cross-sectional view taken along line Y-Y in FIG. 1. FIG. 5 is a cross-sectional view seen from Y-Y direction before use. FIG. 6 is a perspective view showing the absorbent article according to the first embodiment. FIG. 7 is a plan view showing a top absorbent body. FIG. 8(a) is a cross-sectional view taken along line A-A in FIG. 7. FIG. 8(b) is a cross-sectional view taken along line B-B in FIG. 7. FIG. 8(c) is a cross-sectional view taken along line C-C in FIG. 7.

Absorbent Article

As shown in the figures, an absorbent article 1 in this embodiment is elongated in a predetermined direction. The absorbent article 1 includes, a base absorbent body 10 as a substantially rectangular shaped absorbent article main body for absorbing fluid such as menstrual blood, a back face sheet 30 that is provided on the back face of the base absorbent body 10, and a top absorbent body 20 as an absorbent body that is joined to the surface of the base absorbent body 10 and disposed in the center in the width direction of the base absorbent body 10 along the longitudinal direction. The back face sheet 30 is provided in order to prevent leakage of fluid that is to be absorbed by the base absorbent body 10 and the top absorbent body 20 to the back face side.

In the absorbent article 1, a position Z assumed to contact against the bodily discharge opening portion, at which the bodily discharge opening portion is assumed to contact against the absorbent article 1, is positioned closer to the front end side than the center in the longitudinal direction, and on the center line in the width direction of the absorbent article 1. More specifically, the absorbent article 1 is formed such that the length from the position Z assumed to contact against the bodily discharge opening portion to the rear end side is longer than the length from the position Z assumed to contact against the bodily discharge opening portion to the front end side.

The base absorbent body 10 includes an absorbent body base material 12 as another absorbent body in the form of a sheet having a predetermined thickness, in which an absorbent body material 12a as a fluid-absorbent member that has pulverized pulp obtained by pulverizing sheet-like pulp, a superabsorbent polymer, and a thermofusing fiber is wrapped in thin paper (not shown) such as tissue paper, and a surface sheet 14 that is attached to the surface of a center section in the width direction of the absorbent body base material 12. Both of the thin paper and the surface sheet 14 are fluid-permeable sheets. Furthermore, the thin paper is a sheet having openings that are smaller than particles of the superabsorbent polymer, and prevents the superabsorbent polymer from leaking outside of the absorbent body base material 12. A sheet that is softer than the thin paper is used as the surface sheet 14, since it is positioned on the surface side that contacts with the body.

The length in the longitudinal direction of the base absorbent body 10 is a length in which, for example, when worn, the base absorbent body 10 sufficiently covers an area from the position that is approximately 40 mm away in the front direction from the position Z assumed to contact against the bodily discharge opening portion, to the rear position that is at the perineum. The total length of the base absorbent body 10 is set to approximately 220 mm as in so-called regular-sized absorbent articles generally used in the daytime.

The back face sheet 30 is a thermoplastic and fluid-impermeable sheet such as polyethylene or polypropylene. The back face sheet 30 is made sufficiently wider than the base absorbent body 10. Furthermore, on both sides in the width direction of the back face sheet 30, holding sections 32 extended outward in the width direction are formed in a predetermined region in which the position Z assumed to contact against the bodily discharge opening portion is centered in the longitudinal direction. Furthermore, round sealing processing of thermocompression-bonding the outer circumferential edge section of the absorbent article 1 is performed at least on the front end section and the rear end section of the back face sheet 30 and the base absorbent body 10. Here, the end section refers to not only an edge of the outline section, but also the edge and its vicinity. Accordingly, in the permanently joined one end section and the temporarily joined other end section, the edge is not necessarily joined. The same is applied to an "end section" in the following description.

On the back face side of the back face sheet 30, in the vicinity of the region where the surface side has the base absorbent body 10 and the holding sections 32, release sheets 34 (FIG. 2, FIG. 9) are provided via adhesives 35. When using the absorbent article 1, the release sheets 34 are removed, and the back face sheet 30 contacts against the inner side of an undergarment. Also, the holding sections 32 are folded outward, and contact against the outer face of the undergarment. With the adhesives 35 interposed between the back face sheet 30 and the undergarment, the absorbent article 1 is held on the undergarment. Note that, since a release agent has been applied to the release sheets 34, the release sheets 34 can be easily removed from the back face sheet 30 in a state in which the adhesives 35 are left on the back face sheet 30.

In this embodiment, the back face sheet 30 as a sheet member was a thermoplastic and fluid-impermeable sheet made of polyethylene, polypropylene or the like. However, the back face sheet 30 also may be a sheet-like member containing the thermoplastic and fluid-impermeable sheet, for example, formed by layering thin paper, nonwoven fabric, or the like.

The top absorbent body 20 includes, as in the base absorbent body 10, the absorbent body material 12a as a fluid-absorbent member, which is made of pulverized pulp, a super-absorbent polymer, and a thermofusing fiber, and has a fluid-permeable intermediate sheet 16 that has higher fluid retentivity than the surface sheet 14 on the surface side that contacts with the body, with the surface sheet 14 wrapping around the exterior thereof as in the base absorbent body 10. The intermediate sheet 16 is a member that has a higher density than the surface sheet 14 and is highly absorbent due to surface tension. By including the intermediate sheet 16 inside the surface sheet 14, fluid that has permeated the surface sheet 14 is moved toward the intermediate sheet 16 that sucks more fluid than the surface sheet 14.

The width of the top absorbent body 20 is formed narrower than the base absorbent body 10 in the direction that intersects the longitudinal direction. The top absorbent body 20 is disposed on the surface side of the base absorbent body 10 along the longitudinal direction. Furthermore, on the sides of a front end 20a and a rear end 20b in the top absorbent body 20, reinforced sections 25 and 26 are formed that have been reinforced by folding only the surface sheet 14 and performing embossing in a state where an adhesive is interposed between the folded sections of the surface sheet 14. The reinforced sections 25 and 26 do not contain the absorbent body material 12a or the intermediate sheet 16.

Furthermore, in the top absorbent body 20, the reinforced section 26 on the side of the front end 20a is permanently joined to the front end side of the base absorbent body 10, and a portion on the side of the rear end 20b is formed so that it can be moved apart from the base absorbent body 10. Herein, the permanent joining refers to an undetachable state in which the top absorbent body 20 and the base absorbent body 10 are firmly joined to each other so that at least one of the top absorbent body 20 and the base absorbent body 10 is inevitably damaged if they are to be separated from each other intentionally. For example, as shown in FIG. 1, embossing has been performed so as to form deep-groove embossed patterns 19 by thermocompression-bonding. Herein, the method for permanently joining the reinforced section 26 of the top absorbent body 20 and the front end side of the base absorbent body 10 is not necessarily limited to embossing. For example, they can be joined to each other using only a hot-melt adhesive.

The top absorbent body 20 is formed so that when the front end side of the top absorbent body 20 is permanently joined to the front end side of the base absorbent body 10, the absorbent body material 12a is projected outward from the rear edge of the base absorbent body 10. In the portion of the absorbent body material 12a of the top absorbent body 20, which is projected at least from the rear edge of the base absorbent body 10, a face of the top absorbent body 20 at the side of the base absorbent body 10 is included a fluid-impermeable sheet 27 similar to the back face sheet 30 described above. The fluid-impermeable sheet 27 is provided in order to prevent leakage of fluid from the back face side of the top absorbent body 20 that has been worn separately from the base absorbent body 10. The fluid-impermeable sheet 27 may be included in the entire region on the back face side of the top absorbent body 20, or may be included also on the surface side so as to wrap around the rear end side of the top absorbent body 20.

Furthermore, as shown in FIG. 8(b), in a center section in the width direction of the top absorbent body 20, a substantially half region on the rear end side includes a thin wall section 12b, along the longitudinal direction, in which the amount of the absorbent body material 12a is less than that in other portions. With this thin wall section 12b, the top absorbent body 20 is formed so that it can be easily bent along the longitudinal direction so that the surface side continuously forms a peak.

Furthermore, in the reinforced section 25 of the rear end 20b side, on a face on the side of the base absorbent body 10 of a section 25b on the side of the absorbent body material 12a, a hook member 22 is included for fixing a portion on the side of the rear end 20b of the top absorbent body 20 to an undergarment in use. The hook member 22 is, for example, a male member of a mechanical fastener.

In the absorbent article 1, the rear end 20b section of the top absorbent body 20 is projected from the outer circumferential edge, that is, the rear edge, of the base absorbent body 10. Thus, in such state, the total length of the absorbent article 1 is long with poor portability. Further, since the portion on the side of the rear end 20b of the top absorbent body 20 is not joined, for example, the position of the top absorbent body 20 is unstable during production or the like. Accordingly, before use, the rear end side of the top absorbent body 20 is folded, and the reinforced section 25 on the side of the rear end 20b is temporarily joined to a rear end section 10a of the base absorbent body 10. Herein, temporary joining refers to a detachable state in which the base absorbent body 10 and the top absorbent body 20 are joined to each other so that the user can easily detach and separate the top absorbent body 20 from the base absorbent body 10 without impairing the function of the base absorbent body 10 and the top absorbent body 20.

As shown in FIG. 5, the top absorbent body 20 before use is folded to a length that substantially matches to the rear end of the absorbent body material 12a contained in the base absorbent body 10 when unfolded. A folded portion 12c is folded toward the front end side, in a portion closer to the front end than a folding position P, between the top absorbent body 20 and the base absorbent body 10. The folded portion 12c of the top absorbent body 20 is folded again at a folding position Q so that the rear end section 20b of the top absorbent body 20 is slightly projected rearward from the round-sealed rear edge of the rear end section of the base absorbent body 10, and so that the rear end section 20b of the top absorbent body 20 is oriented rearward of the absorbent article 1.

Before use, on the side of the rear end 20b of the top absorbent body 20, the reinforced section 25 is temporarily joined to the round-sealed portion in the rear end section 10a of the base absorbent body 10. The section where the base absorbent body 10 and the reinforced section 25 on the side of the rear end 20b of the top absorbent body 20 overlap is pressed by embossing and thus temporarily joined to each other. However, the hook member 22 also functions to temporarily join the rear end side 20b of the top absorbent body 20 and the surface sheet 14 of the base absorbent body 10 before use. In the description above, the hook member 22 was used for temporary joining, but the method for temporary joining is not limited to this. The method for temporary joining may be merely compression-bonded by embossing, or may be adhered instead of using the hook member 22.

Figure 9:
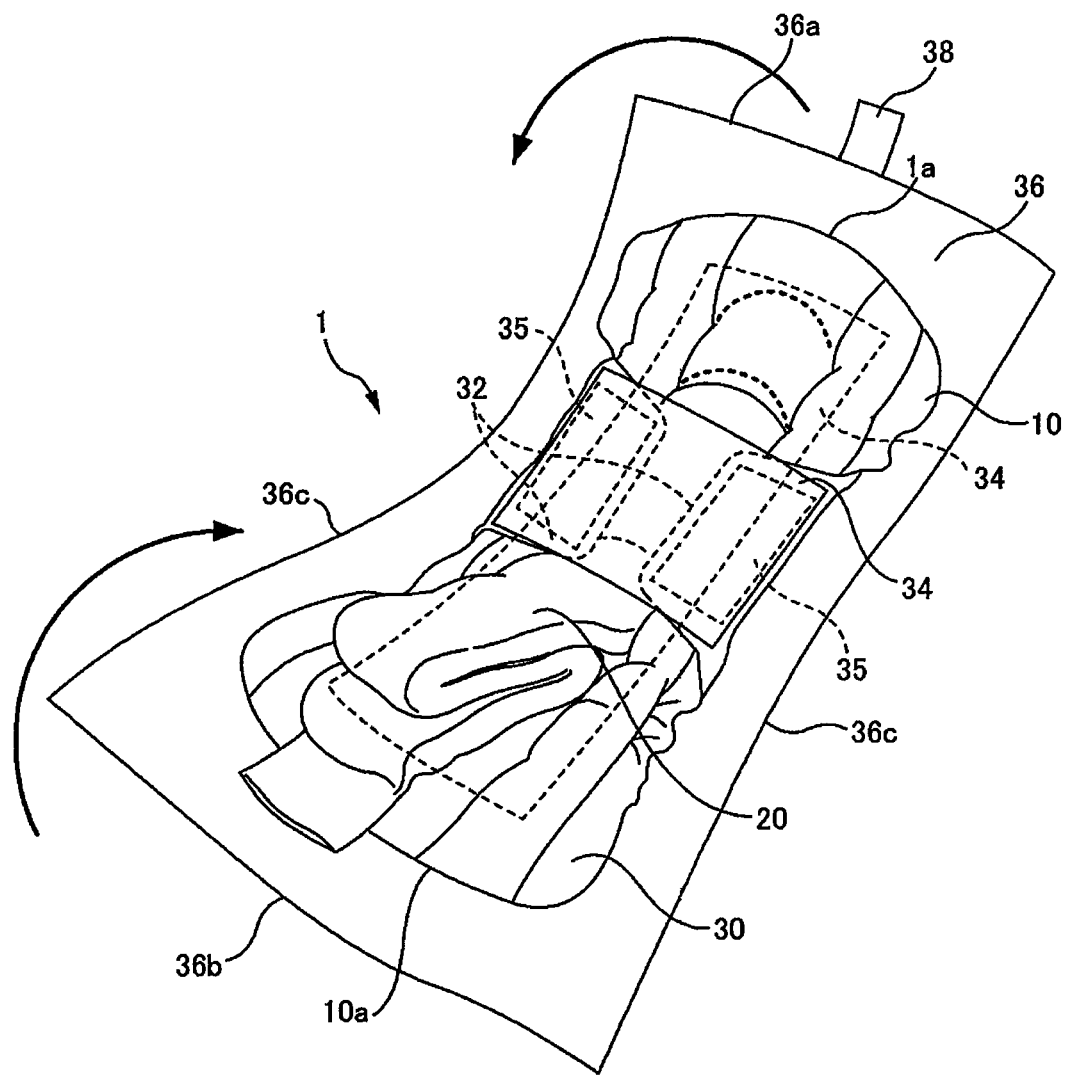
FIG. 9 is a view for illustrating the state in which the absorbent article is wrapped.

Next, the absorbent article 1 in a wrapped state will be described. FIG. 9 is a view for illustrating the manner in which the absorbent article is wrapped.

In the wrapped absorbent article 1, the holding sections 32 are bent toward the surface side, and the release sheets 34 covering the adhesives 35 are included on the holding sections 32 of both sides and the back face side respectively. The absorbent article 1 on which the release sheets 34 have been placed is folded toward the surface side so as to be rolled up along the longitudinal direction together with a rectangular wrapping sheet 36 disposed on the back face side. At that time, an end section of the wrapping sheet 36 on the side of the rear end 10a of the base absorbent body 10 (hereinafter, referred to as a rear end 36b of the wrapping sheet 36) is extended to be longer than the absorbent article 1, with an adhesive slightly applied. When the wrapping sheet 36 is bent together with the absorbent article 1, the end section adheres with very weak adhesion to the side without treatment for detachment of the release sheet 34 provided on the holding sections 32 that have been folded toward the surface side of the top absorbent body 20. A lead tape 38 provided on the side of a front end 36a in the wrapping sheet 36 is attached to the outer face of the wrapping sheet 36 on the side of the rear end 36b that has already been bent together with the absorbent article 1. The wrapping sheet 36 that has been folded together with the absorbent article 1 is sealed by causing edge sections 36c along the longitudinal direction to adhere, and the absorbent article 1 that is contained in the wrapping sheet 36 in the form of a package is supplied to the user.

When the user removes the lead tape 38 of the wrapped absorbent article 1 and opens the wrapping sheet 36, a front end 1a is exposed. When the exposed front end 1a of the absorbent article 1 is peeled from the wrapping sheet 36 having the lead tape 38, the absorbent article 1 can be easily taken out. The taken out absorbent article 1 is disposed at an appropriate position on an undergarment after removing the release sheet 34 on the back face side. Then, the release sheet 34 on the holding sections 32 is removed, and the holding sections 32 are bent toward the undergarment side to be attached to the outer side of the undergarment with the adhesives 35, and thus the absorbent article 1 is fixed to the undergarment. After the undergarment to which the absorbent article 1 is fixed is pulled up toward the body, a portion on the side of the rear end 20b in the reinforced section 25 of the top absorbent body 20, that is, a grasping section 25a is caught and the top absorbent body 20 is pulled up by the user. Accordingly, the temporary joining between the base absorbent body 10 and the top absorbent body 20 is released, and the top absorbent body 20 that has been folded is pulled and unfolded. In the pulled and unfolded top absorbent body 20, the portion including the absorbent body material 12a is projected rearward from the outer circumferential edge (the rear end 10a) of the base absorbent body 10, and is moved apart from the base absorbent body 10.

Subsequently, when the user moves the grasping section 25a in the longitudinal direction (substantially the vertical direction), the position of the top absorbent body 20 is adjusted so that the top absorbent body 20 is in close contact with the bodily groove at the bodily discharge opening portion and its vicinity. In a state that the position of the top absorbent body 20 has been adjusted, the top absorbent body 20 is bent and fixed at the skin-side surface of the back body of the undergarment or the edge section of the undergarment. Accordingly, by disposing the top absorbent body 20 in close contact with the body of the user from the front side to the rear side along the bodily groove, the top absorbent body 20 is positioned so as to preferably contact against the body. The base absorbent body 10 is positioned substantially outside and below the bodily groove.

With the absorbent article according to the first embodiment, the absorbent body material 12a of the top absorbent body 20 is projected in the longitudinal direction from the rear end 10a of the base absorbent body 10. Thus, with the projected top absorbent body 20, fluid can be absorbed in a wider region in the longitudinal direction than the base absorbent body 10. At that time, the base absorbent body 10 is shorter in the longitudinal direction than the top absorbent body 20. Thus, the absorbent article 1 can be made smaller than in a case where the top absorbent body 20 and the base absorbent body 10 are formed having the same length. Accordingly, it is possible to realize the absorbent article 1 that can effectively absorb fluid and that has a small size.

Furthermore, the top absorbent body 20 with a narrow width is projected from the base absorbent body 10. Thus, it is possible to cause fluid flowing down along the groove to be absorbed, by disposing the top absorbent body 20 along and into the bodily groove . Furthermore, the base absorbent body 10 is overlapped with the top absorbent body 20. Thus, fluid flowing down in the vertical direction can be effectively absorbed by the top absorbent body 20 and the base absorbent body.

Moreover, in the absorbent article 1 according to the first embodiment, by detaching the portion of the rear end 20b side in the top absorbent body 20 temporarily joined in a detachable manner, the top absorbent body 20 can be in a state of being joined to the base absorbent body 10 only on the front end 20a side. Furthermore, the detached portion of the rear end 20b side in the top absorbent body 20 can be separated from the base absorbent body 10. Accordingly, for example, it is possible to cause fluid to be absorbed, by separating the top absorbent body 20 from the base absorbent body 10 and placing it reliably and easily in the bodily groove.

Furthermore, a face of the base absorbent body 10 on the side to which the top absorbent body 20 is not joined, that is, the back face includes the back face sheet 30, and at least the projected portion of the top absorbent body 20 includes the fluid-impermeable sheet 27. Thus, in the portion where the top absorbent body 20 and the base absorbent body 10 are overlapped, the back face sheet 30 provided on the base absorbent body 10 can prevent leakage of fluid from the top absorbent body 20 and the base absorbent body 10. In the projected portion of the top absorbent body 20, the fluid-impermeable sheet 27 provided on the projected portion can prevent the leakage.

In this embodiment, an example was described in which the portion on the rear end 20b side of the top absorbent body 20 can be separated from the base absorbent body 10, but there is no limitation to this. For example, the top absorbent body 20 may be undetachably joined at the entire region overlapped with the base absorbent body 10. In this case, in the portion where the top absorbent body 20 and the base absorbent body 10 are overlapped, a configuration can be realized in which fluid is absorbed with both the top absorbent body 20 and the base absorbent body 10, and fluid that has not been absorbed by the top absorbent body 20 can be reliably absorbed with the base absorbent body 10. Moreover, when the portion of the top absorbent body 20 projected from the base absorbent body 10 is positioned along the bodily groove, fluid leaking along the groove can be absorbed with the top absorbent body 20.

Modified Example of the Top Absorbent Body

Figure 10:
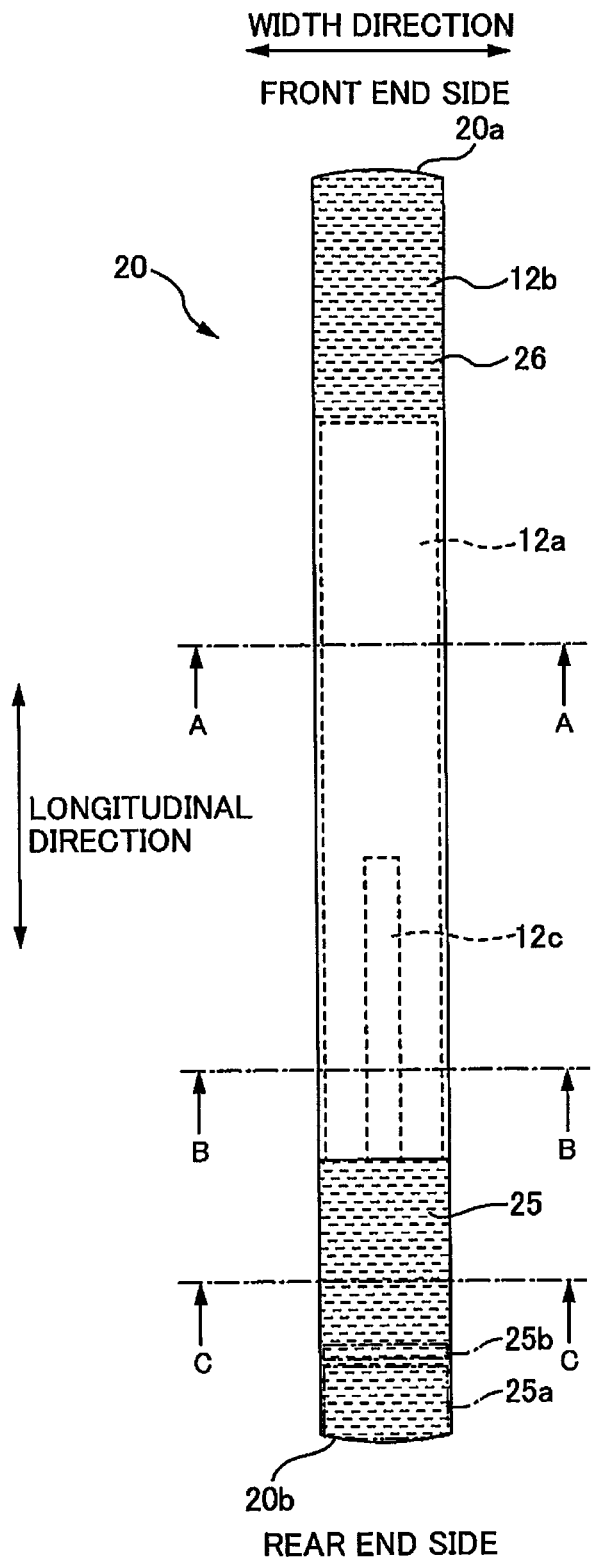
FIG. 10 is a view showing a modified example of the top absorbent body.

FIG. 10 is a view showing a modified example of the top absorbent body.

In the first embodiment, the reinforced section 25 is formed by reinforcing a comparatively narrow region on the rear end side of the top absorbent body 20, and the long absorbent body material 12a is provided in a wide region of the top absorbent body 20. However, there are cases where the top absorbent body 20 is made long, in order to make it possible to easily pick and pull up the rear end side and place the top absorbent body 20 in the bodily groove. Accordingly, the absorbent body material 12a does not have to be longer than necessary, and as long as it is in close contact with the bodily groove and has a capacity that can absorb discharged fluid, for example, as shown in FIG. 10, the region of the absorbent body material 12a may be made short, and the reinforced section 25 may be made long.

Modified Example of the Manner in which the Top Absorbent Body is Folded

Figure 11:
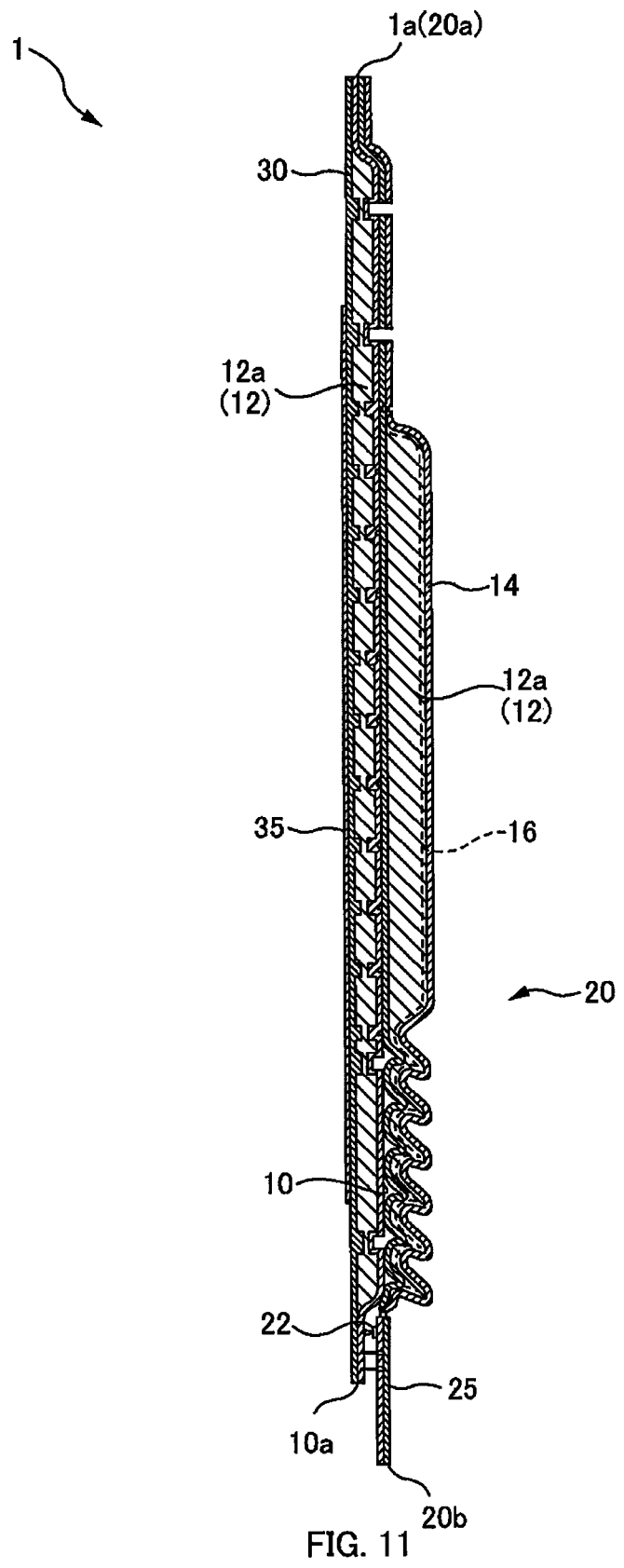
FIG. 11 is a view showing a modified example of the manner in which the top absorbent body is folded.

FIG. 11 is a view showing a modified example of the manner in which the top absorbent body is folded.

In the first embodiment, an example was described in which the portion of the top absorbent body 20 projected from the rear edge of the base absorbent body 10 is folded such that three layers are overlapped in the surface-back face direction in the rear end side of the base absorbent body 10. However, the manner in which the top absorbent body 20 is folded is not limited to this. For example, as shown in FIG. 11, a region may be included in which the top absorbent body 20 is folded in the form of waves on the surface of the base absorbent body 10.

With the absorbent article 1 according to the foregoing embodiment, the absorbent article 1 can be made small by independently folding the top absorbent body 20 of the absorbent article 1, in which the top absorbent body 20 is projected in the longitudinal direction from the outer circumferential edge (rear end) 10a of the base absorbent body 10 and can absorb fluid in a wider region in the longitudinal direction than the base absorbent body 10.

And since the folded top absorbent body 20 is narrow in width, when the top absorbent body 20 is pulled and unfolded to be projected from the base absorbent body 10, the top absorbent body 20 can be placed in the bodily groove with a narrow width and effectively absorb fluid such as menstrual blood. At that time, fluid flowing down along the bodily groove can be absorbed by the unfolded top absorbent body 20, and fluid flowing down in the vertical direction can be effectively absorbed by the base absorbent body 10 and the top absorbent body 20. Accordingly, it is possible to realize the absorbent article 1 that is small and that can absorb fluid in a wider region in the longitudinal direction.

Furthermore, the top absorbent body 20 is folded along the longitudinal direction, and the folded portions are overlapped. Thus, the top absorbent body 20 can be folded neatly and more compactly. Moreover, an end on the side of the folded portions in the top absorbent body 20, that is, the rear end 20b is disposed facing the direction in which the rear end 20b is to be projected from the base absorbent body 10. Thus, it is possible to easily unfold the folded top absorbent body 20, just by pulling the rear end 20b of the top absorbent body 20 in the longitudinal direction. Moreover, in the top absorbent body 20, the end section on the side of the folded region, that is, the rear end 20b section is temporarily joined to the base absorbent body 10 in a detachable manner. Thus, it is possible to easily unfold the top absorbent body 20 by detaching the temporarily joined rear end 20b.

In the foregoing embodiments, a state in which the top absorbent body 20 is folded was described as a state before use, but the top absorbent body 20 also can be used in a folded state. For example, if the body is in a state substantially standing such as daytime and fluid does not have to be absorbed in a wide range, the top absorbent body 20 in a folded state is worn together with the base absorbent body 10 so as to contact against the body.

Furthermore, when the body is lying down such as during sleep and fluid has to be absorbed in a wide range, the top absorbent body 20 is unfolded and worn so as to be placed in the bodily groove. Thus, the absorbent article 1 can be used in two states, namely a state in which the top absorbent body 20 is folded and a state in which the top absorbent body 20 is unfolded, according to the application.

First Modified Example of Absorbent Article According to First Embodiment

Figure 12:
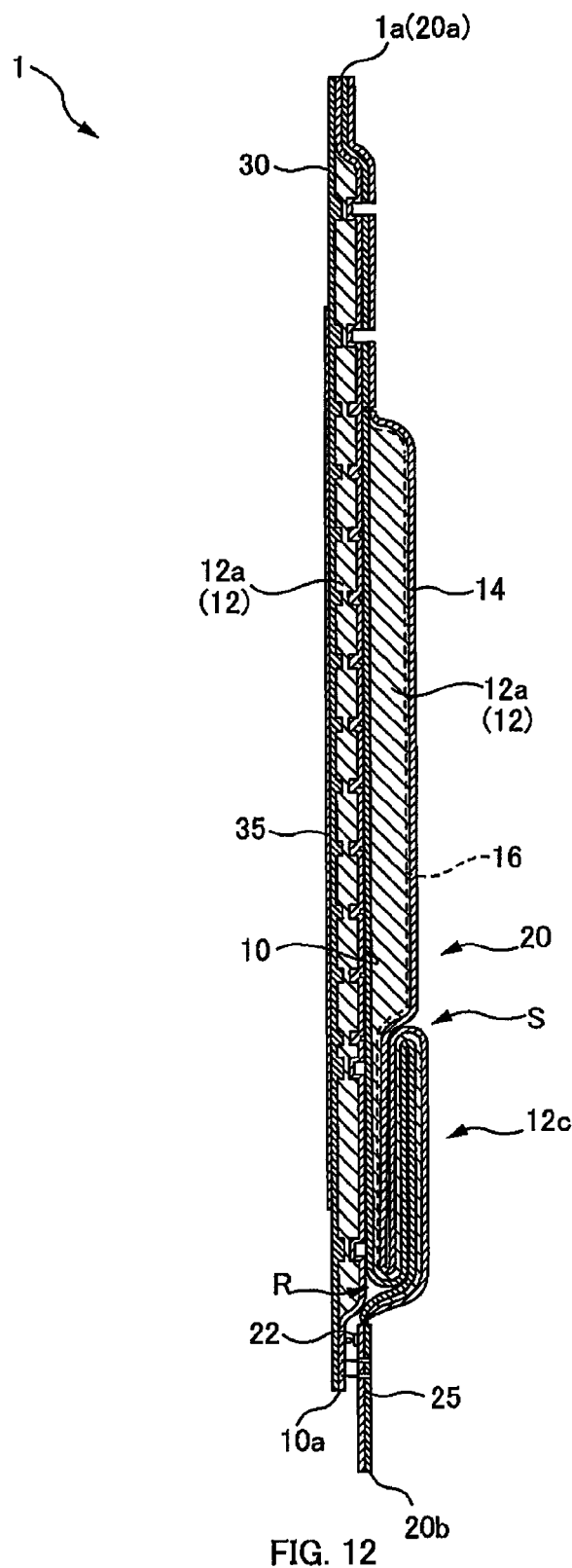
FIG. 12 is a view showing a first modified example of the absorbent article according to the first embodiment.

FIG. 12 is a view showing a first modified example of the absorbent article.

In the first embodiment, an example was described in which only the portion on the front end 20a side in the top absorbent body 20 is permanently joined to the base absorbent body 10 and the rear end side is formed detachable therefrom. However, the top absorbent body 20 whose portion overlapped with the base absorbent body 10 is permanently joined in the longitudinal direction to the surface of the base absorbent body 10 with an adhesive or the like may be projected from the rear edge of the base absorbent body 10. In this case, as shown in FIG. 12, the top absorbent body 20 before use is folded toward the surface side at the vicinity of the rear edge of the portion permanently joined to the base absorbent body 10 that has been unfolded. The folded portion 12c is folded toward the direction of the front end, in a portion closer to the front end side than a folding position R. The folded portion 12c of the top absorbent body 20 is folded again at a folding position S so that the rear end 20b section of the top absorbent body 20 is slightly projected rearward from the round-sealed rear edge of the rear end 10a section of the base absorbent body 10, and so that the rear end 20b section of the top absorbent body 20 is oriented rearward of the absorbent article 1. On the side of the rear end 20b of the top absorbent body 20, the reinforced section 25 is temporarily joined to the round-sealed portion in the rear end 10a section of the base absorbent body 10.

With the absorbent article 1 according to the first modified example of the first embodiment, in the portion where the base absorbent body 10 and the top absorbent body 20 are overlapped, a configuration can be realized in which fluid is absorbed with both the base absorbent body 10 and the top absorbent body 20, and fluid that could not be absorbed with the top absorbent body 20 is reliably absorbed with the base absorbent body 10. Moreover, fluid flowing along the longitudinal direction can be absorbed with the portion of the top absorbent body 20 projected from the base absorbent body 10. Also in this case, the top absorbent body 20 is formed longer than the base absorbent body 10. Thus, there is a possibility that size of the absorbent article 1 itself may increase, and may impair its portability. Accordingly, it is possible to realize the absorbent article 1 with good portability, which is small and can absorb fluid in a wider region in the longitudinal direction.

Second Embodiment

Figure 13:
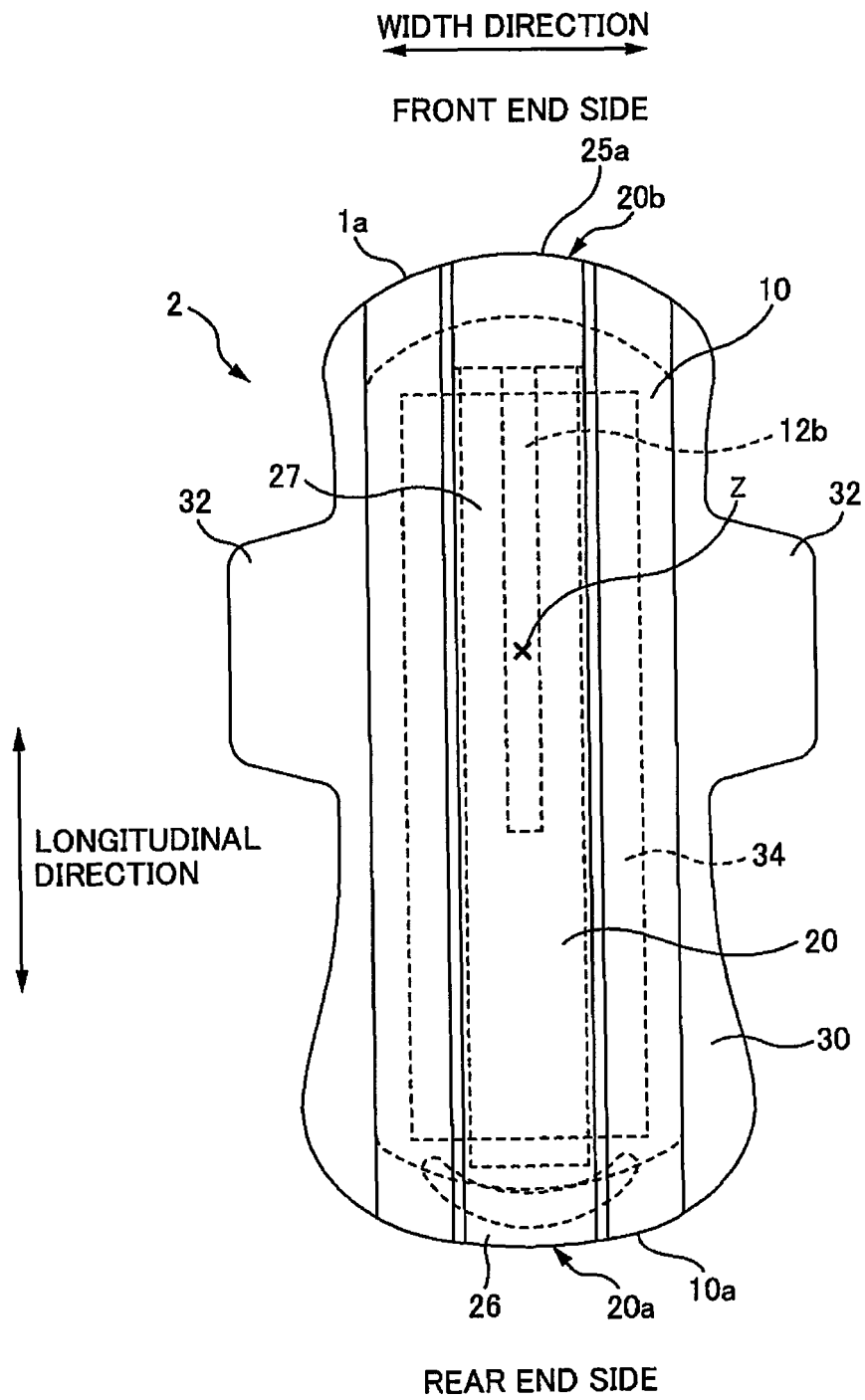
FIG. 13 is a plan view showing the surface side of the absorbent article according to a second embodiment.
Figure 14:
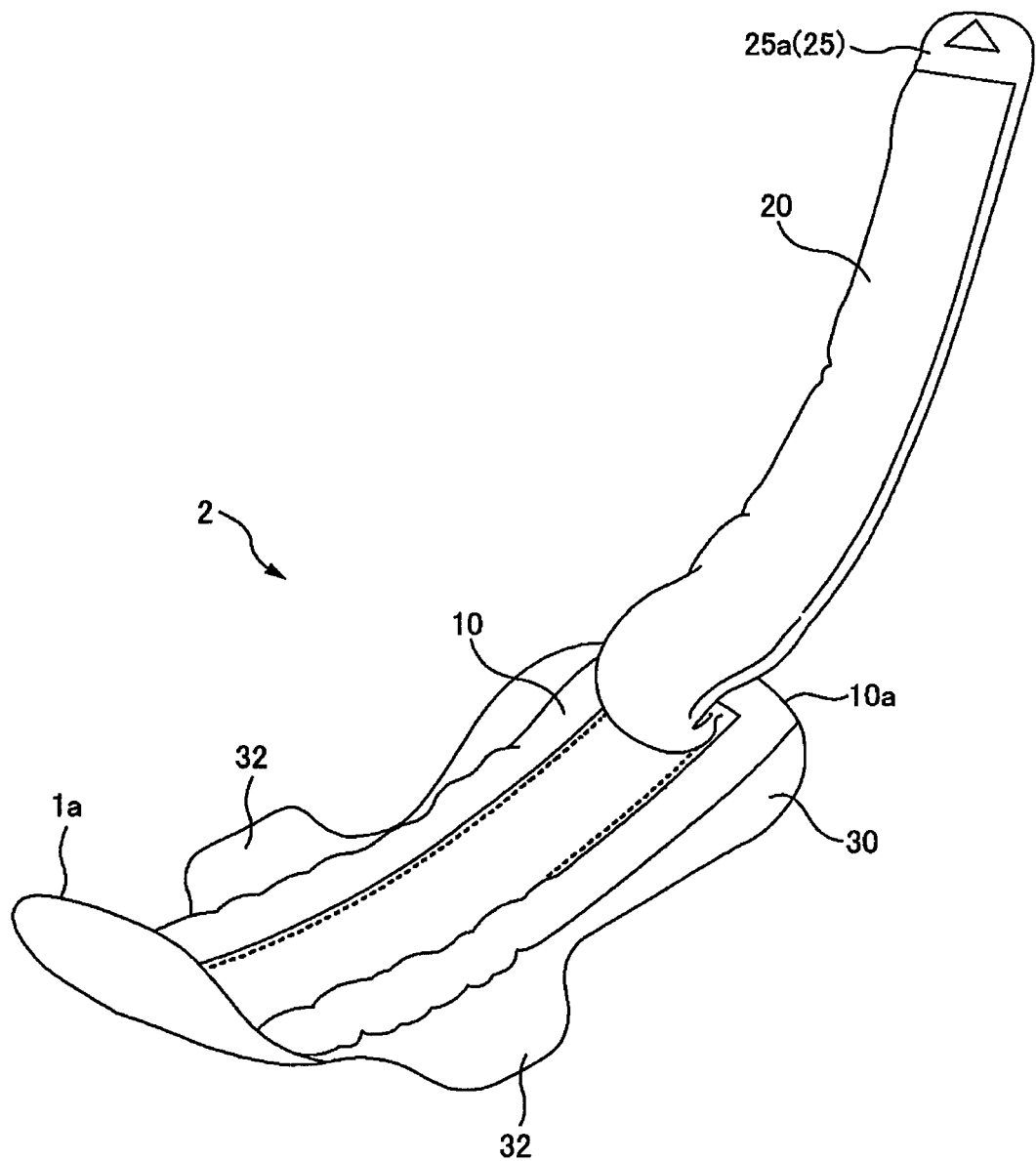
FIG. 14 is a perspective view showing the absorbent article according to the second embodiment.

FIG. 13 is a plan view showing the surface side of an absorbent article according to the second embodiment. FIG. 14 is a perspective view showing the absorbent article according to the second embodiment. Hereinafter, the same elements as in the foregoing embodiment are given the same reference numerals, and a repeated description thereof is omitted.

As shown in FIG. 13, in an absorbent article 2 according to the second embodiment, the length of the top absorbent body 20 joined to the surface of the base absorbent body 10 substantially corresponds with the length of the base absorbent body 10 in the longitudinal direction.

As in the first embodiment, the top absorbent body 20 is disposed along the longitudinal direction on the surface side of the base absorbent body 10. However, in this embodiment, the grasping section 25a side is oriented to the front end side of the base absorbent body 10. Furthermore, the top absorbent body 20 is disposed such that the face side that contacts against the body, that is, the side including the intermediate sheet 16 is opposed to the surface of the base absorbent body 10. Furthermore, the face of the top absorbent body 20 on the opposite side of the base absorbent body 10 includes, throughout the entire region, the fluid-impermeable sheet 27. The reinforced section 26 on the opposite side of the grasping section 25a of the top absorbent body 20 is permanently joined to the rear end side of the base absorbent body 10, and the reinforced section 25 on the side of the grasping section 25a is formed so that it can be moved apart from the base absorbent body 10. Furthermore, before use, the reinforced section 25 on the side of the grasping section 25a of the top absorbent body 20 is temporarily joined to the front end section of the base absorbent body 10.

When using the absorbent article 2 according to the second embodiment, the absorbent article 2 is disposed at an appropriate position on an undergarment after removing the release sheet 34 on the back face side. Then, the release sheet 34 on the holding sections 32 is removed and the holding sections 32 are bent toward the undergarment side to be attached to the outer side of the undergarment with the adhesives 35, thereby the absorbent article 2 is fixed to the undergarment.

Subsequently, by the user grasping the grasping section 25a of the top absorbent body 20 and pulling up the top absorbent body 20, the temporary joining between the base absorbent body 10 and the top absorbent body 20 is released. Furthermore, the user moves the top absorbent body 20 apart from the base absorbent body 10, and moves the end section on the side of the grasping section 25a, as the other end section of the top absorbent body 20, to the opposite side in the longitudinal direction of the permanently joined side end section, that is, the rearward side crossing over the rear end 10a of the base absorbent body 10. At that time, the body contact face that has been opposed to the surface of the base absorbent body 10 is oriented to the body side. Then, the undergarment to which the absorbent article 2 is fixed is pulled up toward the body.

By the user moving the grasping section 25a upward, the position of the top absorbent body 20 is adjusted so that the top absorbent body 20 is in close contact with the bodily groove. After the position has been adjusted, the top absorbent body 20 is bent and fixed at the skin-side surface of the back body of the undergarment or the edge section of the undergarment. Accordingly, the top absorbent body 20 can prevent fluid flowing down along the bodily groove from leaking to a rear portion of the base absorbent body 10.

With the absorbent article 2 according to the second embodiment, before detaching the top absorbent body 20 from the base absorbent body 10, the top absorbent body 20 is not projected from the base absorbent body 10. Further, by moving the base absorbent body 10 that has been detached from the top absorbent body 20 rearward of the permanently joined end section 20a of the top absorbent body 20, the top absorbent body 20 is projected from the rear end 10a of the base absorbent body 10. Accordingly, it is possible to realize the absorbent article 2 that is small before the top absorbent body 20 is detached, and that can effectively absorb fluid with the top absorbent body 20 projected from the base absorbent body 10 after the top absorbent body 20 is detached.

Other Embodiments

In the foregoing embodiments, for the sake of convenience of description, a configuration was described in which one absorbent body base material 12 is included in the center in the width direction of the base absorbent body 10, but there is no limitation to this.

For example, a configuration is also possible in which side absorbent bodies are included along the longitudinal direction in both end sections respectively in the width direction of the base absorbent body 10. Moreover, instead of the side absorbent bodies, a configuration is also possible in which standing gathers are included in both of the end sections respectively.

Figure 15:
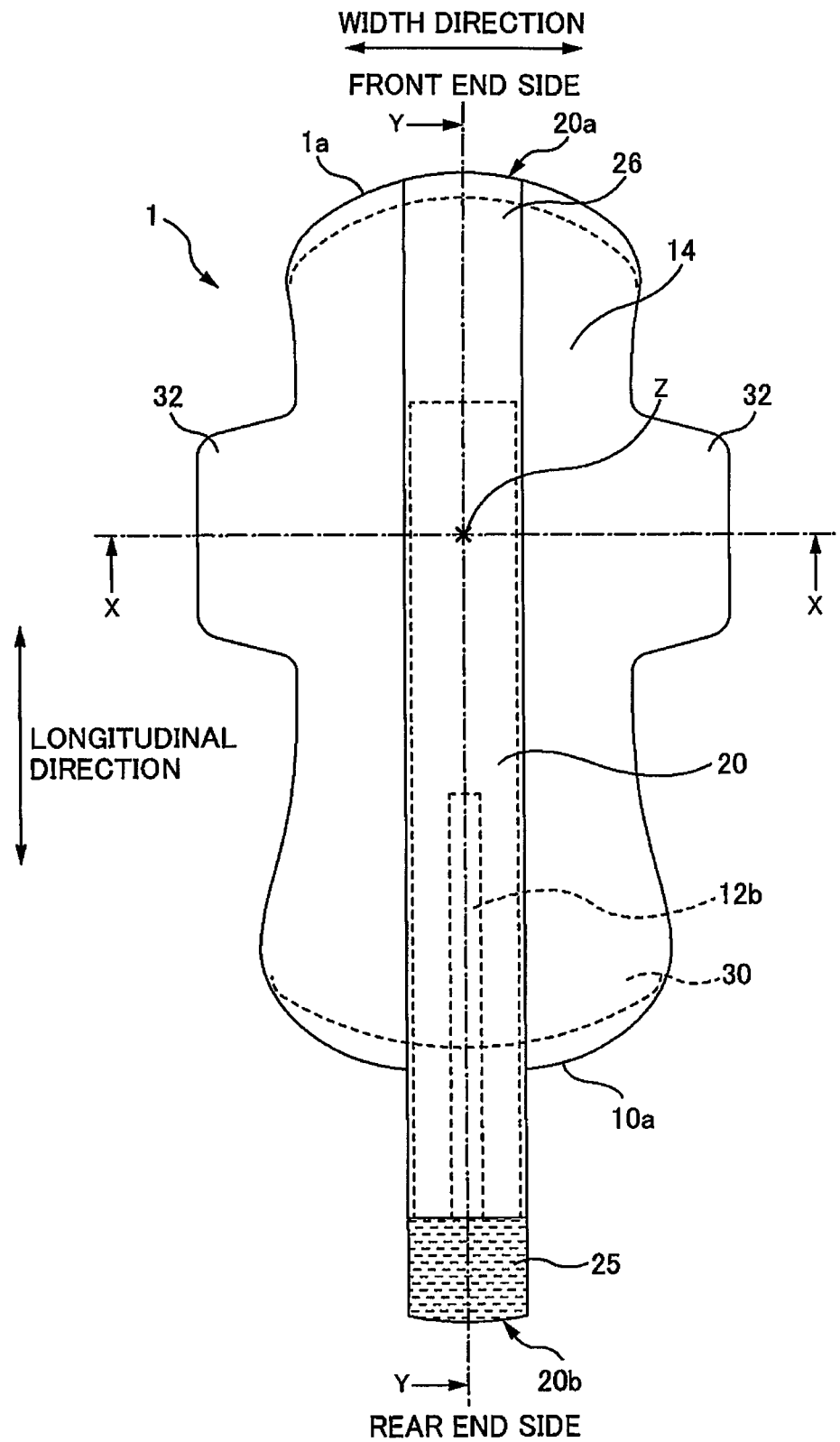
FIG. 15 is a plan view showing the surface side of an absorbent article according to a third embodiment.

In the absorbent articles 1 and 2 according to the first and second embodiments, the base absorbent body 10 as an absorbent article main body had the absorbent body base material 12 and the surface sheet 14, but the absorbent article main body does not necessarily have to include the absorbent body base material 12. FIG. 15 is a plan view showing a second modified example of the absorbent article. As shown in FIG. 15, in the absorbent article 2, the absorbent article main body may be constituted only by the surface sheet 14. Also, the absorbent article main body may have a configuration in which a sheet-like member is layered other than the surface sheet 14.

Furthermore, in the foregoing embodiments, an example was described in which the exterior of the absorbent body material 12a and the intermediate sheet 16 of the top absorbent body 20 is wrapped by the surface sheet 14, and the reinforced sections 25 and 26 are formed on the sides of the both ends 20a and 20b of the top absorbent body 20 by performing embossing in a state where only the surface sheet 14 is folded and caused to adhere. However, in the top absorbent body 20, the absorbent body material 12a may be present also in the reinforced sections 25 and 26.

Furthermore, in the foregoing embodiments, an example was described in which the hook member 22 for fixing the top absorbent body 20 is provided on the rear end side in the top absorbent body 20 in a state where the position of the top absorbent body 20 has been adjusted so as to be in close contact with the bodily groove when the absorbent article 1 is worn. However, a member such as the hook member 22 for fixing the top absorbent body 20 does not necessarily have to be included. In this case, by placing the top absorbent body 20 into the bodily groove, the top absorbent body 20 is sandwiched and held in the bodily groove.

Further, the foregoing embodiments are for the purpose of facilitating understanding of the present invention and are not to be interpreted as limiting the present invention. The invention can of course be altered and improved without departing from the gist thereof, and equivalents are intended to be embraced therein.

The invention claimed is:

1. An absorbent article, comprising:
an absorbent article main body having a longitudinal direction, a width direction, and a thickness direction perpendicular to one another, the absorbent article main body having a first absorbent core and a first surface sheet on a skin facing side of the absorbent article, the skin facing side configured to face a wearer's skin when the absorbent article is worn on the wearer; and
an absorbent body having a second absorbent core for absorbing fluid, and a second surface sheet on the skin facing side,
wherein
the absorbent body overlaps the absorbent article main body along the longitudinal direction,
the absorbent body has a folded portion free of direct attachment to the absorbent article main body,
a first end section of the absorbent body in the longitudinal direction is undetachably joined to a first end portion of the first surface sheet of the absorbent article main body, and
a second end section of the absorbent body, opposite to the first end section of the absorbent body in the longitudinal direction, is detachably joined to a second end portion of the first surface sheet of the absorbent article main body.

2. The absorbent article according to claim 1,
wherein the folded portion is arranged at the second end section and is folded toward the first end section, and
the folded portion overlaps another portion of the absorbent body in the thickness direction.

3. The absorbent article according to claim 2, wherein
the absorbent body has an edge at the second end section, and
said edge projects outward beyond an outer circumferential edge of the absorbent article main body when the second end section of the absorbent body is detachably joined to the second end portion of the first surface sheet of the absorbent article main body.

4. The absorbent article according to claim 1, wherein the absorbent body is adapted to contact the wearer's body in a folded state or in a unfolded state when the absorbent article is worn on the wearer.

5. The absorbent article according to claim 1, wherein
the folded portion has two folds opposite to each other in the longitudinal direction, and
one fold is folded toward the first end section and the other fold is folded toward the second end section to face toward the absorbent article main body.

6. The absorbent article according to claim 1, wherein the first absorbent core of the absorbent article main body overlaps the folded portion in the thickness direction when the second end section of the absorbent body is detachably joined to the second end portion of the first surface sheet of the absorbent article main body.

7. The absorbent article according to claim 1, wherein the absorbent body further comprises a reinforced section at the second end section, and said reinforced section is undetachably joined to the absorbent article main body.

8. The absorbent article according to claim 1, wherein the second end section of the absorbent body is detachably joined to the absorbent article main body by a hook,
the second surface sheet of the absorbent body includes a fluid-impermeable sheet, and
the hook is directly attached to the fluid-impermeable sheet, and does not overlap the second absorbent core of the absorbent body in the thickness direction when the second end section of the absorbent body is detachably joined to the second end portion of the first surface sheet of the absorbent article main body.

9. The absorbent article according to claim 1, wherein the first end section of the absorbent body is joined to an outer circumferential edge section of the absorbent article main body.

10. The absorbent article according to claim 9, wherein the outer circumferential edge section of the absorbent article main body is a round-sealed section.

11. The absorbent article according to claim 1, wherein the first end section of the absorbent body is free of the second absorbent core.

12. The absorbent article according to claim 1, wherein
the first and second end sections of the absorbent body are free of the second absorbent core, and
the second absorbent core is formed between the first end section and the second end section of the absorbent body.

13. The absorbent article according to claim 1, wherein the second end section of the absorbent body is releasably embossed together with the second end portion of the first surface sheet at an embossed region, and the second end section of the absorbent body is detachable from the second end portion of the first surface sheet at the embossed region.

14. The absorbent article according to claim 1, wherein a thickest portion of the absorbent body is thicker than that of the absorbent article main body in the thickness direction.

15. The absorbent article according to claim 1, wherein the first end section of the absorbent body is embossed together with the first end portion of the first surface sheet of the absorbent article main body at an embossed groove, and the first end section of the absorbent body in the longitudinal direction is undetachably joined to the first end portion of the first surface sheet of the absorbent article main body at the embossed groove.

* * * * *